US008383645B2

(12) United States Patent
Patashnik et al.

(10) Patent No.: US 8,383,645 B2
(45) Date of Patent: *Feb. 26, 2013

(54) STABLE LAQUINIMOD PREPARATIONS

(75) Inventors: Shulamit Patashnik, Reut (IL);
Daniella Licht, Givat Shmuel (IL);
Adrian Gilbert, Ra'nanna (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/568,940

(22) Filed: Aug. 7, 2012

(65) Prior Publication Data

US 2012/0302600 A1 Nov. 29, 2012

Related U.S. Application Data

(63) Continuation of application No. 13/166,210, filed on Jun. 22, 2011, now abandoned, which is a continuation of application No. 11/811,810, filed on Jun. 12, 2007, now Pat. No. 7,989,473.

(60) Provisional application No. 60/813,247, filed on Jun. 12, 2006.

(51) Int. Cl.
*A61K 31/47* (2006.01)
*A61K 9/48* (2006.01)

(52) U.S. Cl. ........................................ 514/312; 424/452
(58) Field of Classification Search ........................ None
See application file for complete search history.

(56) References Cited

U.S. PATENT DOCUMENTS

| 3,024,257 | A | 3/1962 | Millar et al. |
| 4,107,310 | A | 8/1978 | Allais et al. |
| 4,547,511 | A | 10/1985 | Eriksoo et al. |
| 4,628,053 | A | 12/1986 | Fries |
| 4,738,971 | A | 4/1988 | Eriksoo et al. |
| 5,716,638 | A | 2/1998 | Touitou |
| 5,912,349 | A | 6/1999 | Sih |
| 6,077,851 | A | 6/2000 | Bjork et al. |
| 6,121,287 | A | 9/2000 | Bjork et al. |
| 6,133,285 | A | 10/2000 | Bjork et al. |
| 6,307,050 | B1 | 10/2001 | Kwiatkowski et al. |
| 6,395,750 | B1 | 5/2002 | Hedlund et al. |
| 6,593,343 | B2 | 7/2003 | Bjork et al. |
| 6,605,616 | B1 | 8/2003 | Bjork et al. |
| 6,613,574 | B2 | 9/2003 | Shimada |
| 6,802,422 | B2 | 10/2004 | Kalvelage et al. |
| 6,875,869 | B2 | 4/2005 | Jansson |
| 7,560,557 | B2 | 7/2009 | Jansson |
| 7,589,208 | B2 | 9/2009 | Jansson et al. |
| 7,884,208 | B2 | 2/2011 | Frenkel et al. |
| 7,989,473 | B2 | 8/2011 | Patashnik et al. |
| 8,178,127 | B2 | 5/2012 | Safadi et al. |
| 2002/0173520 | A1 | 11/2002 | Bjork et al. |
| 2003/0087929 | A1 | 5/2003 | Kimura et al. |
| 2003/0119826 | A1 | 6/2003 | Manning et al. |
| 2003/0124187 | A1 | 7/2003 | Mention et al. |
| 2004/0247673 | A1 | 12/2004 | Fergione et al. |
| 2004/0253305 | A1 | 12/2004 | Luner et al. |
| 2005/0192315 | A1 | 9/2005 | Jansson et al. |
| 2005/0215586 | A1 | 9/2005 | Jansson et al. |
| 2005/0271717 | A1 | 12/2005 | Berchielli et al. |
| 2007/0280891 | A1 | 12/2007 | Tamarkin et al. |
| 2007/0293537 | A1 | 12/2007 | Patashnik et al. |
| 2009/0162163 | A1 | 6/2009 | Safadi et al. |
| 2009/0232889 | A1 | 9/2009 | Jansson et al. |
| 2010/0055072 | A1 | 3/2010 | Grant et al. |
| 2010/0322900 | A1 | 12/2010 | Tarcic et al. |
| 2011/0027219 | A1 | 2/2011 | Tarcic et al. |
| 2011/0034508 | A1 | 2/2011 | Hayardeny |
| 2011/0112141 | A1 | 5/2011 | Frenkel et al. |
| 2011/0118308 | A1 | 5/2011 | Frenkel et al. |
| 2011/0217295 | A1 | 9/2011 | Haviv et al. |
| 2011/0218179 | A1 | 9/2011 | Haviv et al. |
| 2011/0218203 | A1 | 9/2011 | Kaye et al. |
| 2011/0251235 | A1 | 10/2011 | Patashnik et al. |
| 2012/0010238 | A1 | 1/2012 | Piryatinsky |
| 2012/0010239 | A1 | 1/2012 | Fristedt |
| 2012/0225124 | A1 | 9/2012 | Safadi et al. |

FOREIGN PATENT DOCUMENTS

| EP | 0497740 | 8/1992 |
| EP | 1073639 | 2/2001 |
| EP | 1095021 | 5/2001 |
| EP | 1097139 | 5/2001 |
| EP | 1511732 | 3/2005 |
| EP | 1720531 | 11/2006 |
| WO | WO/90/15052 | 12/1990 |
| WO | WO/96/07601 | 3/1996 |
| WO | WO/99/55678 | 11/1999 |
| WO | WO/00/03991 | 1/2000 |
| WO | WO/00/03992 | 1/2000 |
| WO | WO/00/74654 | 12/2000 |
| WO | WO/01/30758 | 5/2001 |
| WO | WO/02/18343 | 3/2002 |
| WO | WO/03/106424 | 12/2003 |
| WO | WO/2005/041940 | 5/2005 |
| WO | WO/2005/074899 | 8/2005 |
| WO | WO/2007/047863 | 4/2007 |
| WO | WO/2007/146248 | 12/2007 |
| WO | WO/2009/082471 | 7/2009 |

OTHER PUBLICATIONS

U.S. Appl. No. 13/312,284, filed Dec. 6, 2011, Tarcic et al.
PCT International Search Report issued Apr. 16, 2007 in connection with PCT International Application No. PCT/US2006/040925, filed Oct. 18, 2006.
PCT International Search Report issued Oct. 23, 2008 in connection with PCT International Application No. PCT/US2007/013721, filed Jun. 12, 2007.
PCT International Search Report issued Feb. 20, 2009 in connection with PCT International Application No. PCT/US08/13890, filed Dec. 19, 2008.
PCT International Search Report issued Apr. 21, 2010 in connection with PCT International Application No. PCT/US2009/055692, filed Sep. 2, 2009.

(Continued)

*Primary Examiner* — Sreeni Padmanabhan
*Assistant Examiner* — Jody Karol
(74) *Attorney, Agent, or Firm* — John P. White; Gary J. Gershik; Cooper & Dunham LLP

(57) ABSTRACT

The invention relates to a pharmaceutical composition comprising a pharmaceutically acceptable salt of N-ethyl-N-phenyl-1,2,-dihydro-4-hydroxy-5-chloro-1-methyl-2-oxoquinoline-3-carboxamide, N-methylglucamine, and a pharmaceutically acceptable carrier.

21 Claims, No Drawings

OTHER PUBLICATIONS

PCT International Search Report issued Nov. 21, 2011 in connection with PCT Int'l Appl. No. PCT/US11/43383, filed Jul. 8, 2011.
PCT International Preliminary Report on Patentability issued Apr. 23, 2008 in connection with PCT international Application No. PCT/US2006/040925, filed Oct. 18, 2006.
PCT International Preliminary Report on Patentability issued Dec. 16, 2008 in connection with PCT International Application No. PCT/US2007/013721, filed Jun. 12, 2007.
PCT international Preliminary Report on Patentability issued Jun. 22, 2010 in connection with PCT International Application No. PCT/US08/13890, filed Dec. 19, 2008.
PCT International Preliminary Report on Patentability issued Mar. 8, 2011 in connection with PCT Int'l Appl. No. PCT/US2009/055692, filed Sep. 2, 2009.
PCT International Preliminary Report on Patentability issued Dec. 20, 2011 in connection with PCT Int'l Appl, No. PCT/US2010/001759, filed Jun. 18, 2010.
Written Opinion of the International Searching Authority issued Apr. 26, 2007 in connection with PCT International Application No. PCT/US06/040925, filed Oct. 18, 2006.
Written Opinion of the International Searching Authority issued Oct. 23, 2008 in connection with PCT International Application No. PCT/US07/013721, filed Jun. 12, 2007.
Written Opinion of the International Searching Authority issued Feb. 20, 2009 in connection with PCT International Application No. PCT/US08/13890, filed Dec. 19, 2008.
Written Opinion of the International Searching Authority issued Apr. 21, 2010 in connection with PCT International Application No. WO/US2009/055692, filed Sep. 2, 2009.
Written Opinion of the International Searching Authority issued Aug. 19, 2010 in connection with PCT International Application No. WO/US2010/001759, fled Jun. 18, 2010.
Written Opinion of the International Searching Authority issued Nov. 21, 2011 in connection with PCT Int'l Appl. No. PCT/US11/43383, filed Jul. 8, 2011.
Supplementary European Search Report issued Aug. 5, 2009 in connection with European Application No. 07809468.7.
Extended European Search Report issued Feb. 16, 2009 in connection with European Application No. 06826297.1.
Extended European Search Report issued Aug. 24, 2009 in connection with European Application No. 07809468.7.
Extended European Search Report issued Jan. 17, 2011 in connection with European Patent Application No. 08864658.3.
Office Action issued by the U.S. Patent and Trademark Office on Jan. 10, 2008 in connection with U.S. Appl. No. 11/583,282.
Office Action issued by the U.S. Patent and Trademark Office on May 13, 2008 in connection with U.S. Appl. No. 11/583,282.
Office Action issued by the U.S. Patent and Trademark Office on Oct. 16, 2008 in connection with U.S. Appl. No. 11/583,282.
Final Office Action issued by the U.S. Patent and Trademark Office on Jul. 23, 2009 in connection with U.S. Appl. No. 11/583,282.
Office Action issued by the U.S. Patent and Trademark Office on Aug. 24, 2009 in connection with U.S. Appl. No. 11/811,810.
Interview Summary issued by the U.S. Patent and Trademark Office on Oct. 20, 2009 in connection with U.S. Appl. No. 11/583,282.
Office Action issued by the U.S. Patent and Trademark Office on Jan. 6, 2010 in connection with U.S. Appl. No. 11/811,810.
Office Action issued by the U.S. Patent and Trademark Office on Jul. 21, 2010 in connection with U.S. Appl. No. 11/811,810.
Notice of Allowance issued by the U.S. Patent and Trademark Office on Sep. 23, 2010 in connection with U.S. Appl. No. 11/583,282.
Final Office Action issued by the U.S. Patent and Trademark Office on Nov. 15, 2010 in connection with U.S. Appl. No. 11/811,810.
Advisory Action mailed by the U.S. Patent and Trademark Office on Feb. 11, 2011 in connection with U.S. Appl. No. 11/811,810.
Advisory Action mailed by the U.S. Patent and Trademark Office on Mar. 29, 2011 in connection with U.S. Appl. No. 11/811,810.
Notice of Allowance issued by the U.S. Patent and Trademark Office on Apr. 8, 2011 in connection with U.S. Appl. No. 11/811,810.
Office Action issued by the U.S. Patent and Trademark Office on Apr. 26, 2011 in connection with U.S. Appl. No. 12/317,104.
Communication Pursuant To Article 94(3) EPC issued by the European Patent Office on May 27, 2009 in connection with European Application No. 06826297.1.
Communication Pursuant To Article 94(3) EPC issued by the European Patent Office on Dec. 15, 2009 in connection with European Application No. 07809468.7.
Examination Report issued by the New Zealand Patent Office on Feb. 3, 2010 in connection with New Zealand Patent Application No. 567088.
Official Communication Pursuant to Article 94(3) EPC issued by the European Patent office on May 7, 2010 in connection with European Patent Application No. 07809468.7.
Official Communication Pursuant to Article 94(3) EPC issued by the European Patent office on Nov. 12, 2010 in connection with European Patent Application No. 07809468.7.
Office Action issued by the Chinese Patent Office on May 25, 2010 in connection with Chinese Patent Application No. 200680039201 (with English translation).
Official Action issued by the Russian Patent Office on Jun. 11, 2010 in connection with Russian Patent Application No. 2008119456 (with English translation).
Office Action issued by the Chinese Patent Office on Jun. 12, 2010 in connection with Chinese Application No. 200780021677.1 (with English translation).
Examination Report issued by the New Zealand Patent Office on Jul. 2, 2010 in connection with New Zealand Patent Application No. 573846.
Office Action issued by the Eurasian Patent Office on Sep. 21, 2010 in connection with Eurasian Application No. 200870599 (with English translation).
Jun. 13, 2008 Communication in Response to May 13, 2009 Office Action issued in connection with U.S. Appl. No. 11/583,282.
Feb. 13, 2009 Communication in Response to Oct. 16, 2008 Office Action issued in connection with U.S. Appl. No. 11/583,282.
Sep. 11, 2009 Communication in Response to Aug. 24, 2009 Office Action in connection with U.S. Appl. No. 11/811,810.
Oct. 23, 2009 Comm. to Make of Record an Interview with Examiner and Resp. to Jul. 23, 2009 Final Office Action, filed in connection with U.S. Appl. No. 11/583,282.
May 1, 2009 Response to Feb. 16, 2009 Extended European Search Report issued by the European Patent Office in connection with European Patent Application No. 06826297.1.
Jan. 13, 2010 Response to Dec. 15, 2009 Office Action issued by the European Patent Office in connection with European Patent Application No. 07809468.7.
Apr. 6, 2010 Amendment in Response to Jan. 6, 2010 Office Action in connection with U.S. Appl. No. 11/811,810.
Oct. 25, 2010 Resp. to Jun. 12, 2010 Office Action issued in connection with Chinese Appl. No. 200780021677.1 (with Eng. lang. draft sent to Chinese assoc. for prep. of Resp.).
Jan. 14, 2011 Amendment under 37 CFR 1.116 in Response to Nov. 15, 2010 Final Office Action filed with the U.S.P.T.O. in connection with U.S. Appl. No. 11/811,810.
Jan. 21, 2011 Resp. to Sep 21, 2010 Office Action issued in connection with Eurasian Appl. No. 200870599 (with Eng. lang. draft sent to Eurasian assoc. for prep. of the Resp.).
Mar. 15, 2011 Amend. In Resp to Feb. 11, 2011 Advisory Action and to Nov. 15, 2010 Final Office Action, filed with the U.S.P.T.O. in connection with U.S. Appl. No. 11/811,810.
Office Action issued by the Ukrainian Patent Office on Apr. 15, 2011 in connection with Ukrainian Patent Application No. 1200900145, filed Jan. 9, 2008.
Nov. 30, 2011 Office Action issued in connection with Chinese Patent Application No. 200780021677.1 (with English translation).
Dec. 16, 2011 Office Action issued in connection with Chinese Patent Application No. 200680039201.6.
Response to Ukrainian Office Action issued in connection with Ukrainian Patent Application No. 2008 06003, national stage of PCT/US2006/040925, filed Oct. 18, 2006.
First Examination Report issued Jan. 11, 2012 in connection with Indian Patent Application No. 1035/MUMNP/2008.
Boneschi M.F. et al. (2003) "Effects of glatiramer acetate on relapse rate and accumulated disability in multiple sclerosis . . . " Mult. Scler. 9(4):349-55 (Abstract).

Brunmark et al. (2002) "The new orally active immunoregulator laquinimod (ABR-215062) effectively inhibits development and relapses . . ." J. of Neuroimmunology 13:163-172.

Furniss et al. (1989) "Recrystallization Techniques" Vogel's Textbook of Practical Organic Chemistry, 5th ed., New York: John Wiley & Sons Inc.

Jansson K. et al. (2006) "Synthesis and Reactivity of Laquinimod, a Quinoline-3-carboxamide . . ." J. Org. Chem. 71(4):1658-1667.

Jönsson Stig et al. (2004) "Synthesis and Biological Evaluation of New 1,2-Dihydro-4-hydroxy-2-oxo-3-quinolinecar boxamides . . ." Journal of Medicinal Chemistry 47:2075-20.

Polman C. et al. (2005) "Treatment with laquinimod reduces development of active MRI lesions in relapsing MS" Neurology 64(6):987-991.

Sandberg-Wolheim et al. (2005) "48-Week Open Safety Study . . . Laquinimod in MS Patients." Therapy-Immunomodulation—Part II, Sep. 30, 2005, 15:30-17:00 (Abstract only).

Thompson (2003) "Investigating the Fundamentals . . . Atomic Force Microscopy" Thesis submitted to the University of Nottingham for the Degree of Doctor of Philosophy, May 2003.

Tuvesson et al. (2005) "Cytochrome P450 3A4 . . . a Novel Immunomodulator." Drug Metabolism and Disposition, 33(6);866-872.

Office Action issued by the U.S. Patent and Trademark Office on Jun. 27, 2012 in connection with U.S. Appl. No. 13/011,187.

Office Action issued by the U.S. Patent and Trademark Office on Jun. 27, 2012 in connection with U.S. Appl. No. 13/011,233.

Office Action issued by the U.S. Patent and Trademark Office on Dec. 1, 2011 in connection with U.S. Appl. No. 13/166,210.

Final Office Action issued by the U.S. Patent and Trademark Office on May 9, 2012 in connection with U.S. Appl. No. 13/166,210.

Office Action issued by the U.S. Patent and Trademark Office on Jun. 29, 2011 in connection with U.S. Appl. No. 12/317,104.

Notice of Allowance issued by the U.S. Patent and Trademark Office on Jan. 6, 2012 in connection with U.S. Appl. No. 12/317,104.

Notice of Allowance issued by the U.S. Patent and Trademark Office on Feb. 8, 2012 in connection with U.S. Appl. No. 12/317,104.

Office Action issued by the U.S. Patent and Trademark Office on Jan. 12, 2012 in connection with U.S. Appl. No. 12/552,663.

Notice of Allowance issued by the U.S. Patent and Trademark Office on Apr. 27, 2012 in connection with U.S. Appl. No. 12/552,663.

European Search Report completed Aug. 10, 2011 in connection with European Patent No. EP 09812145.2.

Decision to Grant Pursuant to Article 97(1) EPC issued by the European Patent Office on Oct. 13, 2011 in connection with European Patent Application No. 07809468.7.

Official Communication Pursuant to Article 71(3) EPC issued by the European Patent office on Oct. 6, 2011 in connection with European Patent Application No. 08864658.3.

Examination Report issued by the Australian Patent Office on Nov. 11, 2011 in connection with Australian Patent Application No. 2006304672.

Examination Report issued by the New Zealand Patent Office on Dec. 22, 2011 in connection with New Zealand Patent Application No. 573846.

Response to Nov. 30, 2011 Office Action filed in connection with Chinese Patent Application No. 200780021677.1(with Eng. lang. draft sent to Chinese assoc. for prep. of Resp.).

Response to Dec. 16, 2011 Office Action filed in connection with Chinese Patent Appliation No. 200680039201.6 (with Eng. lang. draft sent to Chinese assoc. for prep. of Resp.).

21 C.F.R. 211.116—Current Good Manufacturing Practice for Finished Pharmaceuticals, Stability Testing (FR 43 45077, Sep. 29, 1978, as amended 46 FR 56412, Nov. 17, 1981).

Armarego et al. (2003) "Purification of Laboratory Chemicals," 5th Edition, Elsevier, Common Physical Techniques in Purification.

C. Elison, H. Rapoport, R. Laursen, H. W. Elliott, "Effect of Deuteration . . . on Potency . . . of Morphine," Science, Oct. 13, 1961, vol. 134, No. 3485, pp. 1078-1079 (abstract).

Helfenbein, J. Med. Chem., vol. 45, pp. 5806-5808 (2002).

Lab Manual, McMaster University, Chem2006 Lab Manual: Expt. 1, Part B, Introduction (1997-1998), p. 1-9.

Nelson, Drug Metabolism and Disposition, vol. 31, No. 12, pp. 1481-1498 (2003).

"Note for Guidance on Stability Testing: Stability Testing of New Drug Substances and Products" European Medicines Agency, Aug. 2003.

UMSL.edu (http://web.archive.org/web/20000305044205/http://www.umsl.edu/~orglab/pdffiles/practice.pdf (Mar. 5, 2000)).

U.S. Appl. No. 13/560,851, filed Jul. 27, 2012 (Yossi Gilgun and Nora Tarcic).

U.S. Appl. No. 13/560,872, filed Jul. 27, 2012 (Yossi Gilgun and Nora Tarcic).

Sep. 11, 2012 Office Action issued by the Japanese Patent Office in connection with Japanese Patent Application No. 2009-515443.

Feb. 1, 2012 First Office Action issued by the Australian Patent Office in connection with Australian Patent Application No. 2007258366.

Sep. 26, 2012 Response to the Feb. 1, 2012 Office Action in connection with Australian Patent Application No. 2007258366.

Mar. 1, 2012 Amendment in Response to Dec. 1, 2011 Office Action in connection with U.S. Appl. No. 13/166,210.

Oct. 25, 2010 Response to the Jun. 12, 2010 first Office Action issued in connection with Chinese Patent Application No. 200780021677.1.

Oct. 11, 2012 Communication Expressly Abandoning Application filed in connection with U.S. Appl. No. 13/166,201.

Feb. 15, 2012 Response to Nov. 30, 2011 Office Action filed in connection with Chinese Patent Application No. 200780021677.1.

STABLE LAQUINIMOD PREPARATIONS

This application is a continuation of U.S. Ser. No. 13/166,210, filed Jun. 22, 2011, now abandoned which is a continuation of U.S. Ser. No. 11/811,810, filed Jun. 12, 2007, now U.S. Pat. No. 7,989,473, issued Aug. 2, 2011, which claims the benefit of U.S. Provisional Application No. 60/813,247, filed Jun. 12, 2006, the entire contents of each of which in their entireties are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Laquinimod is a compound which has been shown to be effective in the acute experimental autoimmune encephalomyelitis (aEAE) model (U.S. Pat. No. 6,077,851). Its chemical name is N-ethyl-N-phenyl-1,2-dihydro-4-hydroxy-5-chloro-1-methyl-2-oxoquinoline-3-carboxamide, and its Chemical Registry number is 248281-84-7. The processes of synthesis of laquinimod and the preparation of its sodium salt are disclosed in U.S. Pat. No. 6,077,851. An additional process of synthesis of laquinimod is disclosed in U.S. Pat. No. 6,875,869.

Pharmaceutical compositions comprising laquinimod sodium are disclosed in PCT International Application Publication No. WO 2005/074899.

SUMMARY OF THE INVENTION

The subject invention provides a pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof, N-methylglucamine, and a pharmaceutically acceptable carrier.

The subject invention also provides a sealed package comprising the pharmaceutical composition described herein.

The subject invention also provides a sealed package containing a pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof and at least one pharmaceutically acceptable carrier, wherein the sealed package has a moisture permeability of not more than 15 mg/day per liter.

The subject invention also provides a method of treating a subject afflicted with a form of multiple sclerosis comprising administering to the subject the pharmaceutical composition so as to thereby treat the subject.

The subject invention also provides a method for alleviating a symptom of multiple sclerosis in a subject afflicted with a form of multiple sclerosis comprising administering to the subject the pharmaceutical composition thereby alleviating the symptom of multiple sclerosis in the subject.

The subject invention provides a pharmaceutical composition for use in the treatment of, or alleviation of symptoms of, a form of multiple sclerosis.

DETAILED DESCRIPTION OF THE INVENTION

The subject invention provides a pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof, N-methylglucamine, and a pharmaceutically acceptable carrier.

In an embodiment of the pharmaceutical composition the N-ethyl-N-phenyl-1,2,-dihydro-4-hydroxy-5-chloro-1-methyl-2-oxoquinoline-3-carboxamide is in the form of a pharmaceutically acceptable salt.

In another embodiment of the pharmaceutical composition, wherein the pharmaceutically acceptable salt of N-ethyl-N-phenyl-1,2,-dihydro-4-hydroxy-5-chloro-1-methyl-2-oxoquinoline-3-carboxamide is a lithium salt, a sodium salt or a calcium salt.

In another embodiment of the pharmaceutical composition, wherein the pharmaceutically acceptable salt of N-ethyl-N-phenyl-1,2,-dihydro-4-hydroxy-5-chloro-1-methyl-2-oxoquinoline-3-carboxamide is N-ethyl-N-phenyl-1,2,-dihydro-4-hydroxy-5-chloro-1-methyl-2-oxoquinoline-3-carboxamide sodium.

In an embodiment, the pharmaceutical composition is in solid form.

In another embodiment of the pharmaceutical composition the weight ratio of N-methylglucamine to the pharmaceutical salt of N-ethyl-N-phenyl-1,2,-dihydro-4-hydroxy-5-chloro-1-methyl-2-oxoquinoline-3-carboxamide is between 13 to 1 and 15 to 1, or between 13 to 1 and 18 to 1.

In yet another embodiment, the pharmaceutical composition, further comprising a lubricant. Lubricants may be selected from magnesium stearate, sodium stearyl fumarate, talc and hydrogenated vegetable oil.

In yet another embodiment of the pharmaceutical composition, wherein the lubricant is sodium stearyl fumarate.

In yet another embodiment of the pharmaceutical composition, wherein the weight ratio of sodium stearyl fumarate to the pharmaceutically acceptable salt of N-ethyl-N-phenyl-1,2,-dihydro-4-hydroxy-5-chloro-1-methyl-2-oxoquinoline-3-carboxamide is between 9 to 1 and 7 to 1.

In a further embodiment, the pharmaceutical composition, comprising a pharmaceutically acceptable salt of N-ethyl-N-phenyl-1,2,-dihydro-4-hydroxy-5-chloro-1-methyl-2-oxoquinoline-3-carboxamide, mannitol, N-methylglucamine and sodium stearyl fumarate.

In yet a further embodiment, the pharmaceutical composition, comprising, by total weight of the pharmaceutical composition, 0.2% of the pharmaceutically acceptable salt of N-ethyl-N-phenyl-1,2,-dihydro-4-hydroxy-5-chloro-1-methyl-2-oxoquinoline-3-carboxamide, 95.6% mannitol, 3.2% N-methylglucamine, and 1.0% sodium stearyl fumarate.

The invention also provides a pharmaceutical composition characterized in that 1.0% or less of the of N-ethyl-N-phenyl-1,2,-dihydro-4-hydroxy-5-chloro-1-methyl-2-oxoquinoline-3-carboxamide or of the pharmaceutically acceptable salt thereof degrades upon exposure to a 0.15% $H_2O_2$ solution for 40 minutes. This pharmaceutical composition may also be characterized in that less than 0.9%, 0.8%, 0.7%..., or 0.1% of the N-ethyl-N-phenyl-1,2,-dihydro-4-hydroxy-5-chloro-1-methyl-2-oxoquinoline-3-carboxamide or of the pharmaceutically acceptable salt thereof degrades upon exposure to a 0.15% $H_2O_2$ solution for 40 minutes.

The invention also provides a process of making the pharmaceutical composition comprising obtaining N-ethyl-N-phenyl-1,2,-dihydro-4-hydroxy-5-chloro-1-methyl-2-oxoquinoline-3-carboxamide or a pharmaceutically acceptable salt thereof, N-methylglucamine, and a pharmaceutically acceptable carrier, and granulating the N-ethyl-N-phenyl-1,2,-dihydro-4-hydroxy-5-chloro-1-methyl-2-oxoquinoline-3-carboxamide or a pharmaceutically acceptable salt thereof, N-methylglucamine, and a pharmaceutically acceptable carrier by a wet granulation process.

The subject invention also provides a sealed package comprising the pharmaceutical composition described herein.

In an embodiment, the sealed package further comprises a desiccant. Dessicants may be selected from magnesium perchlorate, calcium chloride, silica gel, calcium sulfate, activated alumina and molecular sieve.

In another embodiment of the sealed package, the desiccant is silica gel.

In yet another embodiment of the sealed package of any one of claims 13-15, which after storage at 40° C. and at a relative humidity of 75% for 3 months contains less than 3% of a degradant of sodium stearyl fumarate. This sealed package may also be characterized in that it contains less than 2.9%, 2.8%, 2.7% . . . , or 0.1% of a degradant of sodium stearyl fumarate.

The subject invention also provides a sealed package containing a pharmaceutical composition comprising N-ethyl-N-phenyl-1,2,-dihydro-4-hydroxy-5-chloro-1-methyl-2-oxo-quinoline-3-carboxamide or a pharmaceutically acceptable salt thereof and at least one pharmaceutically acceptable carrier, wherein the sealed package has a moisture permeability of not more than 15 mg/day per liter.

In an embodiment, the sealed package is a blister pack in which the maximum moisture permeability of the blister pack is no more than 0.005 mg/day.

In another embodiment, the sealed package is a bottle. In another embodiment, the bottle is closed with a heat induction liner.

In another embodiment of the sealed package, the pharmaceutically acceptable carrier is an alkaline agent.

In another embodiment, the sealed package further comprises a lubricant.

In another embodiment of the sealed package, the lubricant is sodium stearyl fumarate.

In another embodiment of the sealed package, after exposure of the sealed package to a temperature of 40° C. and a relative humidity of 75% for 3 months the sealed package contains less than 3% of a degradant of sodium stearyl fumarate. This sealed package may also be characterized in that it contains less than 2.9%, 2.9%, 2.7% . . . , or 0.1% of a degradant of sodium stearyl fumarate.

In another embodiment of the sealed package, which after exposure of the sealed package to a temperature of 40° C. and a relative humidity of 75% for 3 months the sealed package contains less than 1% of a degradant of sodium stearyl fumarate. This sealed package may also be characterized in that it contains less than 0.9%, 0.8%, 0.7% . . . , or 0.1% of a degradant of sodium stearyl fumarate.

In another embodiment, the sealed package comprises an HDPE bottle.

In another embodiment, the sealed package further comprises a desiccant.

In another embodiment of the sealed package, the desiccant is silica gel.

The subject invention also provides a method of treating a subject afflicted with a form of multiple sclerosis comprising administering to the subject the pharmaceutical composition so as to thereby treat the subject described herein.

The subject invention also provides a method for alleviating a symptom of multiple sclerosis in a subject afflicted with a form of multiple sclerosis comprising administering to the subject the pharmaceutical composition described herein thereby alleviating the symptom of multiple sclerosis in the subject.

The subject invention also provides a pharmaceutical composition described herein for use in the treatment of, or alleviation of symptoms of, a form of multiple sclerosis.

The subject invention also provides the use of the pharmaceutical composition for the manufacture of a medicament for treating, or alleviating a symptom of, a form of multiple sclerosis.

A pharmaceutically acceptable salt of laquinimod as used in this application includes lithium, sodium, potassium, magnesium, calcium, manganese, copper, zinc, aluminum and iron.

An "alkaline agent" is any pharmaceutically acceptable excipient which raises the pH of the pharmaceutical composition in which it is used. If the pharmaceutical composition is in solid form, its pH can be measured by dissolving it in an amount of water per amount of composition, and then measuring the pH using conventional methods, e.g., by dissolving 2 g of the composition in 4 g of de-ionized water, and then measuring the pH of the resulting slurry.

1-Deoxy-1-(methylamino)-D-glucitol, also known as N-methylglucamine or meglumine, is prepared from D-glucose and methylamine (Merck Index, 12th ed. (1996), page 1038). Meglumine forms salts with acids and complexes with metals. Id.

Multiple sclerosis is a chronic, inflammatory CNS disease characterized pathologically by demyelination in the brain and spinal cord. There are five main forms of multiple sclerosis: 1) benign multiple sclerosis; 2) relapsing-remitting multiple sclerosis (RR-MS); 3) secondary progressive multiple sclerosis (SP-MS); 4) primary progressive multiple sclerosis (PP-MS); and 5) progressive-relapsing multiple sclerosis (PR-MS). Symptoms of multiple sclerosis include the frequency of relapses, the frequency of clinical exacerbation, or the accumulation of physical disability.

EXPERIMENTAL DETAILS

Example 1

Laquinimod Sodium Capsules Comprising Sodium Carbonate

Capsules were made which corresponded to 0.3 mg of laquinimod acid (LA) per capsule and 0.6 mg of laquinimod acid per capsule using the following excipients as shown in Table 1:

TABLE 1

| Component | 0.3 mg LA/capsule | 0.6 mg LA/capsule |
| --- | --- | --- |
| Laquinimod Sodium | 0.32 | 0.64 |
| Mannitol USP | 151.08 | 302.16 |
| Sodium carbonate anhydrous USP | 4.55 | 9.10 |
| Sodium Stearyl fumarate NF | 1.6 | 3.2 |
| Total Weight | 157.55 | 315.1 |

The capsules were made using the following method:
1. Mannitol and 99% of the total desired anhydrous sodium carbonate were placed into a high shear granulating mixer and were mixed for 30 seconds.
2. A solution of laquinimod sodium, 1% of the total desired anhydrous sodium carbonate and purified water was prepared in a mixer until dissolved.
3. The solution from step 2 was added to the contents of the high shear granulating mixer of step 1 and was mixed to form a suitable granulate.

4. The granulate was dried in a fluid bed dryer with the inlet air temperature of 50° C. and outlet air temperature of 40° C.
5. The dry granulate was milled using a 0.8 mm screen, and blended with sodium stearyl fumarate.
6. The mixture from step 5 was filled into size 1 hard gelatin capsules (0.5 mL volume) for the 0.6 mg laquinimod acid dose and into size 3 hard gelatin capsules (0.3 mL volume) for the 0.3 mg of laquinimod acid dose.

Example 2

Laquinimod Sodium Capsules Comprising Meglumine

Capsules were made which corresponded to 0.3 mg of laquinimod acid (LA) per capsule and 0.6 mg of laquinimod acid per capsule using the following excipients as shown in Table 2:

TABLE 2

| Component | 0.3 mg LA/capsule | 0.6 mg LA/capsule |
| --- | --- | --- |
| Laquinimod Sodium | 0.32 | 0.64 |
| Mannitol USP | 151.08 | 302.16 |
| Meglumine USP | 5.0 | 10.0 |
| Sodium Stearyl fumarate NF | 1.6 | 3.2 |
| Total Weight | 158 | 316 |

The capsules were made using the following method:
1. Mannitol and 90% of the total desired meglumine were placed into a high shear granulating mixer and were mixed for 30 seconds.
2. A solution of laquinimod sodium, 10% of the total desired meglumine and purified water was prepared in a mixer until dissolved.
3. The solution from step 2 was added to the contents of the high shear granulating mixer of step 1 and mixed to form a suitable granulate.
4. The granulate was dried in a fluid bed dryer with the inlet air temperature of 50° C. and outlet air temperature of 40° C.
5. The dry granulate was milled using a 0.8 mm screen, and blended with sodium stearyl fumarate.
6. The mixture from step 5 was filled into size 1 hard gelatin capsules (0.5 mL volume) for the 0.6 mg laquinimod acid dose and into size 3 hard gelatin capsules (0.3 mL volume) for the 0.3 mg of laquinimod acid dose.

Example 3a

Water Vapor Permeability Testing of Packaging

The following containers were tested:
A. Round high density polyethylene (HDPE) 40 mL containers (40 cc W/M Rd, Manufactured by Drug Plastics & Glass Co., Lot 009213) sealed with 33 mm Caps with Aluminum heat induction liners (CL, Argus-Loc, 33 mm, 400, white, 0.020" WLP/SG-529 Top Tab "E.O.S." Red—Manufactured by Owens-Brockway Plastics—Brookville, Pa.)
B. Blister Packaging using soft Aluminum (Aluminum thin strip gauge 45 micron, soft temper, plain, dull side lacquer laminated to a 25 micron OPA film, bright side lacquer laminated to a 60 micron PVC film manufactured by Alcan, Singen, Germany) with silver aluminum (Blisterfoil reel: 151 mm, stove lacquer LD2000, aluminum hard temper foil, heatseal coating LX4DP, manufactured by Hueck Folien Pirkmuhle.)
C. HDPE 50 mL containers (DUMA® manufactured by Superfos Pharma Pack, Vaelose, Denmark. Article No. 035050-300) sealed with polypropylene caps (28 mm with 2 g silica gel manufactured by Superfos Pharma Pack, Vaelose, Denmark. Article no. 02829D-300T.)
D. HDPE 30 mL containers (manufactured by Quality Container, Ypsilanti, Mich. Item No. W.0030B33400WH09T) sealed with child-resistant caps (33 mm) (33 mm Saf-Cap III-A with pulp and polyex primary liner, and secondary liner PS-22 0.002" Eva Wax Type Pressure Sensitive Adhesive Coated on a 0.020 Tekni-Foam Printed "SFYP", manufactured by Van Blarcom, Closures, Inc. Brooklyn, N.Y.)

Containers A, C and D

The moisture permeability of the containers A, C and D was measured according to United States Pharmacopoeia, $29^{th}$ edition, U.S. Pharmacopoeia <671> (Multiple-unit containers for capsules and tablets) as follows:

Desiccant Preparation: A quantity of 4- to 8-mesh, anhydrous calcium chloride was placed in a shallow container, taking care to exclude any fine powder, then dried at 110° C. for 1 hour, and cooled in a desiccator.

Procedure: 12 containers of a uniform size and type were selected, the sealing surfaces were cleaned with a lint-free cloth, and each container was closed and opened 30 times. The closure was applied firmly and uniformly each time the container was closed. Screw-capped containers were closed with a torque that was within the range of tightness specified in Table 3. Desiccant was added to 10 of the containers, designated Test Containers, filling each to within 13 mm of the closure. Each was closed immediately after adding desiccant, applying the torque designated in Table 3 when closing screw-capped containers. To each of the remaining 2 containers, designated Controls, add a sufficient number of glass beads to attain a weight approximately equal to that of each of the Test Containers, and close, applying the torque designated in Table 3 when closing screw-capped containers. The weight of the individual containers so prepared was recorded to the nearest mg; and stored at 75°±3% relative humidity and a temperature of 23° C.±2° C. After 336±1 hours (14 days), the weight of the individual containers was recorded in the same manner. 5 empty containers of the same size and type as the containers under test were completely filled with water or a noncompressible, free-flowing solid such as well-tamped fine glass beads, to the level indicated by the closure surface when in place. The contents of each were transferred to a graduated cylinder, and the average container volume was determined, in mL. The rate of moisture permeability, in mg per day per liter, was calculated by the formula:

$$(1000/14V)[(TF-TI)-(CF-CI)]$$

in which V was the volume, in mL, of the container, (TF−TI) was the difference, in mg, between the final and initial weights of each test container, and (CF−CI) was the difference, in mg, between the average final and average initial weights of the 2 controls. As containers used for drugs being dispensed on prescription, the containers so tested were tight containers as not more than one of the 10 test containers exceeded 100 mg per day per liter in moisture permeability, and none exceeded 200 mg per day per liter.

TABLE 3

| Closure Diameter[1] (mm) | Suggested Tightness Range with Manually Applied Torque[2] (inch-pounds) |
|---|---|
| 8 | 5 |
| 10 | 6 |
| 13 | 8 |
| 15 | 5-9 |
| 18 | 7-10 |
| 20 | 8-12 |
| 22 | 9-14 |
| 24 | 10-18 |
| 28 | 12-21 |
| 30 | 13-23 |
| 33 | 15-25 |
| 38 | 17-26 |
| 43 | 17-27 |
| 48 | 19-30 |
| 53 | 21-36 |
| 58 | 23-40 |
| 63 | 25-43 |
| 66 | 26-45 |
| 70 | 28-50 |
| 83 | 32-65 |
| 86 | 40-65 |
| 89 | 40-70 |
| 100 | 45-70 |
| 110 | 45-70 |
| 120 | 55-95 |
| 132 | 60-95 |

[1]The torque designated for the next larger closure diameter was to be applied in testing containers having a closure diameter intermediate to the diameters listed.
[2]The torque values refer to application, not removal, of the closure.

Container B

The moisture permeability of the container B was measured according to United States Pharmacopoeia, 29$^{th}$ edition, U.S. Pharmacopoeia <671> Method II (Single-unit containers and unit-dose containers for capsules and tablets) as follows:

Desiccant Preparation: Suitable desiccant pellets were dried at 110° C. for 1 hour prior to use. Pellets weighing approximately 400 mg each and having a diameter of approximately 8 mm were used.

Procedure: A sufficient number of packs were sealed, such that not fewer than 4 packs and a total of not fewer than 10 unit-dose containers or blisters filled with 1 pellet in each unit are tested. A corresponding number of empty packs were sealed, each pack containing the same number of unit-dose containers or blisters as used in the test packs, to provide the controls. All of the containers were stored at 75%±3% relative humidity and at a temperature of 23° C.±2° C. After 24 hours, and at each multiple thereof, the packs from the chamber were removed, and allowed to equilibrate for about 45 minutes. The weights of the individual packs were recorded, and returned to the chamber. The control packs were weighed as a unit, and the total weight was divided by the number of control packs to obtain the average empty pack weight. The average rate of moisture permeation was calculated, in mg per day, for each unit-dose container or blister in each pack taken by the formula:

$$(1/NX)[(WF-WI)-(CF-CI)]$$

in which N was the number of days expired in the test period (beginning after the initial 24-hour equilibration period); X was the number of separately sealed units per pack; (WF−WI) was the difference, in mg, between the final and initial weights of each test pack; and (CF−CI) was the difference, in mg, between the average final and average initial weights of the control packs, the rates being calculated to two significant figures.

Results

The following were the results for the permeability testing of each container. The R value (rate of moisture permeability) for each container is expressed in Table 4 in terms of mg/L/day.

TABLE 4

| Sample Number | Package A | Package C | Package D |
|---|---|---|---|
| 1 | 52.82 | 0 | 38.88 |
| 2 | 8.34 | 0 | 32.4 |
| 3 | 4.17 | 1.17 | 17.82 |
| 4 | 4.17 | 0 | 51.84 |
| 5 | 4.17 | 1.17 | 25.92 |
| 6 | 2.78 | 0 | 12.96 |
| 7 | 12.51 | 1.17 | 25.92 |
| 8 | 4.17 | 0 | 14.58 |
| 9 | 8.34 | 0 | 35.64 |
| 10 | 12.51 | 0 | 30.78 |

The arithmetic mean value of moisture permeability for 10 containers of type A, C and D in mg/L/day was determined to be 11.4, 0.351 and 28.7, respectively.

The packaging type B was tested according to USP <671>Method II. No pack tested exceeded 0.5 mg moisture permeability per day, and was thus classified as Class A according to USP <671> Method II.

Example 3b

Appearance of Laquinimod Sodium Capsules in Various Packaging

Laquinimod sodium capsules (0.3 mg of LA/capsule) prepared according to Examples 1 and 2 were packaged in packaging types A (35 capsules per package), B (7 capsules, each individually sealed, per blister package), C (35 capsules per package) and D (40 capsules per package) as described in Example 3a.

The sealed packages were stored at 40° C. at 75% relative humidity.

1-2 packages were opened per time point for packages A, C, and D. 5 blister packages (35 capsules) were opened per time point for package B. Only sealed packages were evaluated at each time point.

The appearance of all of the capsules at time zero was normal. The appearance of the capsules at various time points is listed in Table 5:

TABLE 5

| Time (months) | Packaging | Example 1 | Example 2 |
|---|---|---|---|
| 1 | D | Normal | Spots |
| 2 | D | Spots | No data |
| 3 | D | No Data | Deteriorated |
| 3 | A, B and C | Normal | Normal |
| 4 | D | Deteriorated | No Data |

These results indicate that packaging D was unacceptable for storing the capsules of Examples 1 and 2.

Example 3c

Stability of Laquinimod Sodium Capsules in Various Packaging

Capsules (0.3 mg of LA/capsule) from Examples 1 and 2 were packaged in packaging of types A, B and C:

The sealed packages were stored at 40° C. at 75% relative humidity.

1-2 packages were opened per time point for packages A, C, and D. 5 blister packages (35 capsules) were opened per time point for package B. Only sealed packages were evaluated at each time point.

At certain time points, a peak identified to be fumaric acid was observed in chromatographic analysis of some of the capsules. The fumaric acid was present in the formulation as a result of the degradation of sodium stearyl fumarate. The percent degradation of sodium stearyl fumarate was calculated based on the amount of fumaric acid present. The percent degradation of sodium stearyl fumarate (w/w, degraded sodium stearyl fumarate/starting sodium stearyl fumarate) is listed in Table 6.

TABLE 6

| Time (Months) | Packaging | Example 1 (% degradation) | Example 2 (% degradation) |
|---|---|---|---|
| 0 | (none) | 0.2 | <0.1 |
| 1 | A | 10.5 | 0.4 |
| 1 | B | 5.2 | 0.3 |
| 1 | C | 0.1 | 0.2 |
| 2 | A | 21.3 | 1.3 |
| 2 | B | 9.0 | 0.7 |
| 2 | C | 0.1 | 0.1 |
| 3 | A | 39.2 | 2.8 |
| 3 | 3 | 12.7 | 1 |
| 3 | C | 0.2 | <0.1 |

Example 4

Forced Degradation of Laquinimod Sodium Capsules

Laquinimod sodium capsules manufactured according to Examples 1 and 2 were exposed to 0.15% $H_2O_2$ solution for 40 minutes.

The amount of sodium laquinimod in each capsule after exposure was measured using a chromatographic assay, and the percent decrease is listed below:
Formulation of Example 1: 28.5% decrease.
Formulation of Example 2: 0.7% decrease.
Results The use of meglumine as an excipient in sodium laquinimod prevented oxidation-related degradation of laquinimod sodium under forced conditions.
Discussion The use of meglumine in the formulations of Example 2 inhibits the degradation of sodium stearyl fumarate at 40° C. and 75% relative humidity such that 10% or less degradation occurs after 3 months as compared to analogous formulations without meglumine. This indicates that the use of meglumine in laquinimod sodium formulations increases stability.

Furthermore, the use of meglumine reduces the degradation of the laquinimod sodium in a formulation. Specifically, when exposed to 0.15% $H_2O_2$ solution for 40 minutes the formulation with meglumine of Example 2 exhibited less than 2.5% of laquinimod sodium degradation as compared to an analogous formulation without meglumine under the same conditions.

In addition, as seen from the results after 3 months, packaging laquinimod sodium compositions in the presence of a desiccant such as silica gel increases stability of the formulations. Specifically, the presence of a desiccant in the packaging results in 20% or less (in some cases 0.5%) degradation of sodium stearyl fumarate occurring as compared to packaging without desiccant under the same conditions and time interval.

WO 2005/074899 discloses that laquinimod is susceptible to chemical degradation in solid state. Accordingly, WO 2005/074899 teaches a method of preparing laquinimod sodium for pharmaceutical use by dissolving laquinimod base in the neutral form in a solution of an alkaline reacting component such as sodium carbonate, thus producing laquinimod sodium. The manufacturing processes disclosed in WO 2005/074899 all keep laquinimod base in contact with water.

The disclosure of WO 2005/074899 thus indicates that there is no problem when laquinimod is in contact with water.

Therefore, when addressing the question of packaging laquinimod, it would appear irrelevant whether a package for laquinimod is permeable to moisture. Herein, however, it has been shown that solid laquinimod formulations are indeed sensitive to moisture and degrade more rapidly in the presence of moisture. To solve this newly recognized problem, the subject invention provides that laquinimod should be packaged in a package with low moisture permeability.

The invention claimed is:

1. A pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof, N-methylglucamine, and a pharmaceutically acceptable carrier, wherein the amount of N-methylglucamine is such that it reduces the degradation of N-ethyl-N-phenyl-1,2,-dihydro-4-hydroxy-5-chloro-1-methyl-2-oxoquinoline-3-carboxamide or a pharmaceutically acceptable salt thereof in the composition relative to a corresponding formulation without N-methylglucamine.

2. The pharmaceutical composition of claim 1, wherein the N-ethyl-N-phenyl-1,2,-dihydro-4-hydroxy-5-chloro-1-methyl-2-oxoquinoline-3-carboxamide is in the form of a pharmaceutically acceptable salt.

3. The pharmaceutical composition of claim 1, wherein the pharmaceutically acceptable salt of N-ethyl-N-phenyl-1,2,-dihydro-4-hydroxy-5-chloro-1-methyl-2-oxoquinoline-3-carboxamide is a lithium salt, a sodium salt or a calcium salt.

4. The pharmaceutical composition of claim 1, wherein the pharmaceutically acceptable salt of N-ethyl-N-phenyl-1,2,-dihydro-4-hydroxy-5-chloro-1-methyl-2-oxoquinoline-3-carboxamide is N-ethyl-N-phenyl-1,2,-dihydro-4-hydroxy-5-chloro-1-methyl-2-oxoquinoline-3-carboxamide sodium.

5. The pharmaceutical composition of claim 1 in solid form.

6. The pharmaceutical composition of claim 1, further comprising a lubricant.

7. The pharmaceutical composition of claim 6, wherein the lubricant is sodium stearyl fumarate.

8. The pharmaceutical composition of claim 7, wherein the weight ratio of sodium stearyl fumarate to the pharmaceutically acceptable salt of N-ethyl-N-phenyl-1,2,-dihydro-4-hydroxy-5-chloro-1-methyl-2-oxoquinoline-3-carboxamide is between 9 to 1 and 7 to 1.

9. The pharmaceutical composition of claim 1, comprising a pharmaceutically acceptable salt of N-ethyl-N-phenyl-1,2,-dihydro-4-hydroxy-5-chloro-1-methyl-2-oxoquinoline-3-carboxamide, mannitol, N-methylglucamine and sodium stearyl fumarate.

10. The pharmaceutical composition of claim 1 characterized in that 1.0% or less of the of N-ethyl-N-phenyl-1,2,-dihydro-4-hydroxy-5-chloro-1-methyl-2-oxoquinoline-3- carboxamide or of the pharmaceutically acceptable salt thereof degrades upon exposure to a 0.15% $H_2O_2$ solution for 40 minutes.

11. A process of making the pharmaceutical composition of claim 1, comprising obtaining N-ethyl-N-phenyl-1,2,-dihydro-4-hydroxy-5-chloro-1-methyl-2-oxoquinoline-3-carboxamide or a pharmaceutically acceptable salt thereof, N-methylglucamine, and a pharmaceutically acceptable carrier, and granulating the N-ethyl-N-phenyl-1,2,-dihydro-4-hydroxy-5-chloro-1-methyl-2-oxoquinoline-3-carboxamide or a pharmaceutically acceptable salt thereof, N-methylglucamine, and a pharmaceutically acceptable carrier by a wet granulation process.

12. A sealed package comprising the pharmaceutical composition of claim 1.

13. The sealed package of claim 12, further comprising a desiccant.

14. The sealed package of claim 12, wherein the desiccant is silica gel.

15. The sealed package of claim 12, which after storage at 40° C. and at a relative humidity of 75% for 3 months contains less than 3% of a degradant of sodium stearyl fumarate.

16. A sealed package containing a pharmaceutical composition comprising N-ethyl-N-phenyl-1,2,-dihydro-4-hydroxy-5-chloro-1-methyl-2-oxoquinoline-3-carboxamide or a pharmaceutically acceptable salt thereof and at least one pharmaceutically acceptable carrier, wherein the sealed package has a moisture permeability of not more than 15 mg/day per liter.

17. A method of treating a subject afflicted with a form of multiple sclerosis comprising administering to the subject the pharmaceutical composition of claim 1 so as to thereby treat the subject.

18. A method for alleviating a symptom of multiple sclerosis in a subject afflicted with a form of multiple sclerosis comprising administering to the subject the pharmaceutical composition of claim 1 thereby alleviating the symptom of multiple sclerosis in the subject.

19. The pharmaceutical composition of claim 1, wherein the amount of N-methylglucamine is such that it reduces the degradation of N-ethyl-N-phenyl-1,2,-dihydro-4-hydroxy-5-chloro-1-methyl-2-oxoquinoline-3-carboxamide or a pharmaceutically acceptable salt thereof in the composition to less than 2.5% of the degradation in the corresponding formulation without N-methylglucamine.

20. The pharmaceutical composition of claim 1, wherein the degradation is oxidation-related degradation.

21. The pharmaceutical composition of claim 1, wherein the amount of degradation is calculated by measuring the percent decrease in the amount of sodium laquinimod in the composition.

* * * * *